(12) United States Patent
Audousset et al.

(10) Patent No.: US 7,927,380 B2
(45) Date of Patent: Apr. 19, 2011

(54) COMPOSITION FOR OXIDATION DYEING OF KERATIN FIBERS COMPRISING AT LEAST ONE FATTY SUBSTANCE, AT LEAST ONE OXIDATION BASE, AT LEAST ONE DYE PRECURSOR, AT LEAST ONE OXIDIZING AGENT, AND OPTIONALLY AT LEAST ONE ALKALINE AGENT, AND PROCESSES AND KITS THEREWITH

(75) Inventors: Marie-Pascale Audousset, Asnieres (FR); Isabelle Schlosser, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,531

(22) Filed: Dec. 18, 2009

(65) Prior Publication Data

US 2010/0162493 A1 Jul. 1, 2010

Related U.S. Application Data

(60) Provisional application No. 61/150,919, filed on Feb. 9, 2009.

(30) Foreign Application Priority Data

Dec. 19, 2008 (FR) .................................... 08 07309

(51) Int. Cl.
A61Q 5/10 (2006.01)
C07D 231/44 (2006.01)

(52) U.S. Cl. ............. 8/405; 8/406; 8/410; 8/435; 8/573; 8/617; 8/690; 8/692; 548/369.1

(58) Field of Classification Search .............. 8/405, 406, 8/410, 435, 573, 617, 690, 692; 548/369.1
See application file for complete search history.

(56) References Cited

U.S. PATENT DOCUMENTS

| | | |
|---|---|---|
| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie et al. |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,766,977 B2 | 8/2010 | Cottard et al. |

(Continued)

FOREIGN PATENT DOCUMENTS

CA 1 268 421 5/1990

(Continued)

OTHER PUBLICATIONS

French Search Report for FR 0807309, dated Aug. 3, 2009. English language abstract of DE 10 2006 012 575 A1, Feb. 8, 2007.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,536, filed Dec. 18, 2009.
Copending U.S. Appl. No. 12/642,543, filed Dec. 18, 2009.

(Continued)

*Primary Examiner* — Eisa B Elhilo
(74) *Attorney, Agent, or Firm* — Finnegan, Henderson, Farabow, Garrett & Dunner

(57) ABSTRACT

The disclosure relates to a composition for the oxidation dyeing of keratin fibers comprising: A) at least one fatty substance wherein the at least one fatty substance is present in an amount greater than or equal to 25% by weight relative to the total weight of the composition; B) at least one oxidation base chosen from diaminopyrazolones and acid-addition salts thereof; C) at least one additional dye precursor other than the oxidation base in B); D) at least one oxidizing agent; and optionally E) at least one alkaline agent.

25 Claims, No Drawings

U.S. PATENT DOCUMENTS

| | | |
|---|---|---|
| 7,799,095 B2 | 9/2010 | Mario et al. |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | Legrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1* | 1/2008 | Cottard et al. ............ 8/411 |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 A1 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 | 12/2004 |
| EP | 1 550 656 B1 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 A2 | 12/2007 |
| EP | 1 902 703 | 3/2008 |
| EP | 1 927 377 A1 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |

| | | |
|---|---|---|
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.

Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

COMPOSITION FOR OXIDATION DYEING OF KERATIN FIBERS COMPRISING AT LEAST ONE FATTY SUBSTANCE, AT LEAST ONE OXIDATION BASE, AT LEAST ONE DYE PRECURSOR, AT LEAST ONE OXIDIZING AGENT, AND OPTIONALLY AT LEAST ONE ALKALINE AGENT, AND PROCESSES AND KITS THEREWITH

This application claims benefit of U.S. Provisional Application No. 61/150,919, filed Feb. 9, 2009, the contents of which are incorporated herein by reference. This application also claims benefit of priority under 35 U.S.C. §119 to French Patent Application No. 0807309, filed Dec. 19, 2008, the contents of which are also incorporated herein by reference.

The present patent application relates to a composition for the oxidation dyeing of keratin fibers.

Dyeing of keratin fibers, such as human hair with dye compositions comprising oxidation dyes, for example, oxidation dye precursors and coloration modifiers, may be generally known.

Oxidation dye precursors, which are generally known as oxidation bases, are compounds that may be initially colorless or faintly colored, which, when combined with oxidizing products, may give rise to colored compounds and dyes via a process of oxidative condensation. They can be compounds such as ortho- or para-phenylenediamines, ortho- or para-aminophenols and heterocyclic bases.

It is also known that the shades obtained with these oxidation bases may be varied by combining them with couplers or coloration modifiers, the latter generally being chosen from meta-diaminobenzenes, meta-aminophenols, meta-diphenols and certain heterocyclic compounds such as indole compounds.

The variety of molecules used as oxidation bases and couplers makes it possible to obtain a wide range of colors.

The "permanent" coloration obtained using these oxidation dyes, which is also known as oxidation dyeing, should moreover satisfy at least one of a certain number of requirements. For instance, it should have no toxicological drawbacks, it should be able to produce shades with the desired intensity and it should have good resistance to external agents such as light, bad weather, washing, permanent-waving, perspiration and/or rubbing.

The dyes should also allow gray hair to be covered and, moreover, they should be as unselective as possible, i.e. they should produce the smallest possible coloration differences along the same keratin fiber, which generally comprises differently sensitized (i.e. damaged) areas between its end and its root.

Many attempts have been made in the field of hair dyeing to improve the dyeing properties, for example using adjuvants. However, the selection of these adjuvants can be difficult since they should improve the dyeing properties of dye compositions without harming the other properties of these compositions. For example, these adjuvants should not harm the lightening properties of keratin fibers or the dye application properties.

Accordingly, one aspect of the present disclosure relates to novel compositions for the oxidation dyeing of keratin fibers, which can avoid at least one of the drawbacks of the prior art. For example, the present disclosure relates to compositions for the oxidation dyeing of keratin fibers, which can have improved dyeing properties and which can be easy to mix and apply, which for example, do not run, but can remain satisfactorily localized at the point of application. The term "improved dyeing properties" means, for example, an improvement in the level of power/intensity and/or uniformity of the dyeing.

Thus, one aspect of the present disclosure, is a composition for the oxidation dyeing of keratin fibers, for example human keratin fibers, such as the hair, comprising:
A) at least one fatty substances, wherein the at least one fatty substance is present in an amount greater than or equal to 25% by weight relative to the total weight of the composition;
B) at least one oxidation base chosen from diaminopyrazolones and acid-addition salts thereof;
C) at least one additional dye precursor other than the oxidation base in B);
D) at least one oxidizing agent; and optionally
E) at least one alkaline agent.

The composition in accordance with the present disclosure exhibits improved dyeing properties. For example, the composition of the disclosure leads to colorations that have good power and/or intensity and good uniformity of the color along the fiber between the end and the root of the hair (also known as coloration selectivity) and/or good chromaticity. The composition of the disclosure can be applied without difficulty to keratin fibers, without running. This composition may also produce less degradation of the keratin fibers in the course of the dyeing process.

Finally, the coloration obtained using the compositions of the disclosure can be fast and resistant to the various external attacking factors to which keratin fibers may be subjected.

One aspect of the present disclosure is also a process for dyeing keratin fibers, comprising:
providing a composition comprising:
A) at least one fatty substance, wherein the at least one fatty substance is present in an amount greater than or equal to 25% by weight relative to the total weight of the composition;
B) at least one oxidation base chosen from diaminopyrazolones and acid-addition salts thereof;
C) at least one additional dye precursor other than the oxidation base in B);
D) at least one oxidizing agent; and optionally
E) at least one alkaline agent; and
applying the composition to the keratin fibers for a time that is sufficient to develop the desired coloration.

Another aspect of the disclosure is a multi-compartment device or dyeing "kit" comprising: a first compartment comprising (A) at least one fatty substance; a second compartment comprising (B) at least one oxidation base chosen from diaminopyrazolones and acid-addition salts thereof, (C) at least one additional dye precursor other than the at least one oxidation base in (B), and optionally (E) at least one alkaline agent; and a third compartment comprising (D) at least one oxidizing agent and optionally at least one fatty substance.

Another aspect of the disclosure is a multi-compartment device or dyeing "kit" comprising: a first compartment comprising a composition comprising (A) at least one fatty substance and (D) at least one oxidizing agent; and a second compartment comprising (B) at least one oxidation base chosen from diaminopyrazolones and acid-addition salts thereof, (C) at least one additional dye precursor other than the oxidation base in (B), and optionally (E) at least one alkaline agent. This device may be equipped with a means for applying the desired mixture to the hair, such as the devices described in patent FR-A-2 586 913 in the name of the Applicant.

Another aspect of the disclosure is a multi-compartment device or dyeing "kit" comprising: a first compartment comprising a composition comprising (A) at least one fatty substance, (B) at least one oxidation base chosen from diaminopyrazolones and acid-addition salts thereof, (C) at least one additional dye precursor other than the at least one oxidation base in (B), and optionally (E) at least one alkaline agent; and a second compartment comprising (D) at least one oxidizing agent.

As has been mentioned, the composition of the disclosure comprises at least one fatty substance.

The term "fatty substance" means an organic compound that is insoluble in water at ordinary temperature (25° C.) and at atmospheric pressure (760 mmHg) (solubility of less than 5%, for example 1%, such as 0.1%). They may contain in their structure a sequence of at least two siloxane groups or at least one hydrocarbon-based chain containing at least 6 carbon atoms. In addition, the fatty substances may be soluble in organic solvents under the same temperature and pressure conditions, for instance chloroform, ethanol, benzene or decamethylcyclopentasiloxane.

According to the present disclosure, the fatty substances may be different from fatty acid.

The fatty substances may be, for example, chosen from lower alkanes, fatty alcohols, fatty acid esters, fatty alcohol esters, oils, such as non-silicone mineral, plant, animal or synthetic oils, non-silicone waxes and silicones.

According to at least one embodiment, the fatty alcohols, fatty esters and fatty acids have at least one linear or branched, saturated or unsaturated hydrocarbon-based group containing 6 to 30 carbon atoms, which is optionally substituted, for example, with at least one hydroxyl groups (such as 1 to 4). If they are unsaturated, these compounds may comprise one to three conjugated or nonconjugated carbon-carbon double bonds.

According to at least one embodiment, the lower alkanes comprise from 6 to 16 carbon atoms and are linear or branched, and optionally cyclic. For example, the alkanes may be chosen from hexane, dodecane, and isoparaffins, for instance isohexadecane and isodecane.

Examples of oils that may be used in the composition of the disclosure include:
  hydrocarbon-based oils of animal origin, such as perhydrosqualene;
  hydrocarbon-based oils of plant origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;
  linear or branched hydrocarbons of mineral or synthetic origin, such as liquid paraffins, and derivatives thereof, petroleum jelly, liquid petroleum jelly, polydecenes, hydrogenated polyisobutenes such as PARLEAM®;
  fluoro oils such as perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition of the disclosure may be non-oxyalkylenated. They may be saturated or unsaturated, linear or branched, and contain 6 to 30 carbon atoms, for example, from 8 to 30 carbon atoms, such as cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol.

Examples of the waxes that may be used in the composition of the disclosure include carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials, for example, marine waxes such as the product sold by the company Sophim under the reference M82, and polyethylene waxes or polyolefin waxes in general.

The fatty acids that may be used in the composition of the disclosure may be saturated or unsaturated and may contain from 6 to 30 carbon atoms, for example, from 9 to 30 carbon atoms. They may be, for example, chosen from myristic acid, palmitic acid, stearic acid, behenic acid, oleic acid, linoleic acid, linolenic acid and isostearic acid.

The esters may be esters of saturated or unsaturated, linear or branched C1-C26 aliphatic mono- or polyacids and of saturated or unsaturated, linear or branched C1-C26 aliphatic mono- or polyalcohols, the total carbon number of the esters being greater than or equal to 10.

Examples of monoesters include dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

According to at least one embodiment, esters of C4-C22 dicarboxylic or tricarboxylic acids and of C1-C22 alcohols, and/or esters of mono-, di- or tricarboxylic acids and of C2-C26 di-, tri-, tetra- or pentahydroxy alcohols, may be used.

Examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

According to at least one embodiment, the esters may be chosen from ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate.

The composition may also comprise, as fatty ester, sugar esters and diesters of C6-C30, for example C12-C22, fatty acids. The term "sugar" as used in the disclosure means oxygen-bearing hydrocarbon-based compounds containing alcohol functions, with or without aldehyde or ketone functions, and which contain at least 4 carbon atoms. These sugars may be monosaccharides, oligosaccharides or polysaccharides.

Examples of suitable sugars include sucrose (or saccharose), glucose, galactose, ribose, fructose, maltose, mannose, arabinose, xylose and lactose, and derivatives thereof, for example, alkyl derivatives, such as methyl derivatives, for instance methylglucose.

The sugar esters of fatty acids may be chosen, for example, from the esters or mixtures of esters of sugars described above and of linear or branched, saturated or unsaturated C6-C30, for example, C12-C22, fatty acids. If they are unsaturated, these compounds may comprise one to three conjugated or nonconjugated carbon—carbon double bonds.

According to at least one embodiment, the esters may be chosen from mono-, di-, tri-, tetraesters and polyesters, and mixtures thereof.

The esters may be chosen, for example, from oleates, laurates, palmitates, myristates, behenates, cocoates, stearates, linoleates, linolenates, caprates and arachidonates, or mixtures thereof such as, oleo-palmitate, oleo-stearate and palmito-stearate mixed esters.

According to at least one embodiment, the esters may be chosen from monoesters and diesters and for example, sucrose, glucose or methylglucose mono- or dioleates, stearates, behenates, oleopalmitates, linoleates, linolenates and oleostearates.

An example that may be mentioned is the product sold under the name GLUCATE® DO by the company Amerchol, which is a methylglucose dioleate.

Examples of esters or mixtures of esters of sugar and of fatty acid may also include:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, or sucrose monolaurate;
  the products sold under the name Ryoto Sugar Esters, for example referenced B370 and corresponding to sucrose behenate formed from 20% monoester and 80% di-triester-polyester; and
  the sucrose mono-dipalmito-stearate sold by the company Goldschmidt under the name TEGOSOFT® PSE.

The silicones that may be used in the cosmetic compositions of the present disclosure may be volatile or nonvolatile, cyclic, linear or branched silicones, which may be unmodified or modified with organic groups, having a viscosity ranging from $5 \times 10^{-6}$ to $2.5 \ m^2/s$ at 25° C., for example, $1 \times 10^{-5}$ to $1 \ m^2/s$.

The silicones that may be used in accordance with the disclosure may be in the form of oils, waxes, resins or gums.

According to at least one embodiment, the silicone is chosen from polydialkyl-siloxanes, for example, polydimethylsiloxanes (PDMS), and organomodified polysiloxanes comprising at least one functional group chosen from poly(oxyalkylene) groups, amino groups and alkoxy groups.

The organopolysiloxanes are defined in greater detail in Walter Noll's "Chemistry and Technology of Silicones" (1968) Academic Press. They can be volatile or nonvolatile.

When they are volatile, the silicones may be, for example, chosen from those having a boiling point of ranging from 60° C. to 260° C., such as, (i) cyclic polydialkylsiloxanes containing from 3 to 7, for example, 4 to 5 silicon atoms. These are, for example, octamethylcyclotetrasiloxane sold in particular under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and SILBIONE® 70045 V 5 by Rhodia, and mixtures thereof.

Exemplary mention may also be made of cyclocopolymers of the dimethylsiloxane/methylalkylsiloxane type, such as VOLATILE SILICONE® FZ 3109 sold by the company Union Carbide, of formula:

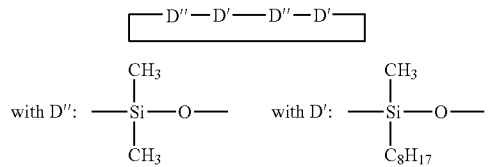

Exemplary mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6} \ m^2/s$ at 25° C. An example may be decamethyltetrasiloxane sold in particular under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Nonvolatile polydialkylsiloxanes, polydialkylsiloxane gums and resins, polyorganosiloxanes modified with organofunctional groups above, and mixtures thereof, may also be used.

These silicones may be for example, chosen from polydialkylsiloxanes, such as polydimethylsiloxanes containing trimethylsilyl end groups. The viscosity of the silicones is measured, for example, at 25° C. according to ASTM standard 445 Appendix C.

Examples of polydialkylsiloxanes include, but are not limited to, the following commercial products:
  the SILBIONE® oils of the 47 and 70 047 series or the MIRASIL® oils sold by Rhodia, for instance the oil 70 047 V 500 000;
  the oils of the MIRASIL® series sold by the company Rhodia;
  the oils of the 200 series from the company Dow Corning, such as DC200 with a viscosity of 60 000 $mm^2/s$;
  the VISCASIL® oils from General Electric and certain oils of the SF series (SF 96, SF 18) from General Electric.

Exemplary mention may also be made of polydimethylsiloxanes containing dimethylsilanol end groups known under the name DIMETHICONOL (CTFA), such as the oils of the 48 series from the company Rhodia.

In this category of polydialkylsiloxanes, exemplary mention may also be made of the products sold under the names ABIL WAX® 9800 and 9801 by the company Goldschmidt, which are poly(C1-C20)dialkylsiloxanes.

The silicone gums that can be used in accordance with the disclosure are for example, polydialkylsiloxanes, such as polydimethylsiloxanes, with high number-average molecular weight ranging from 200,000 to 1,000,000, used alone or as a mixture in a solvent. The solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mixtures that can be used in accordance with the disclosure include products such as:
  mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
  mixtures formed from a polydimethylsiloxane gum with a cyclic silicone, such as the product SF 1214 SILICONE FLUID from the company General Electric, which is an SF 30 gum corresponding to a dimethicone, having a number-average molecular weight of 500 000, dissolved in the oil SF 1202 SILICONE FLUID corresponding to decamethylcyclopentasiloxane;
  mixtures of two PDMSs with different viscosities, for example, of a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of $5 \times 10^{-6}$ m²/s. This product may contain 15% SE 30 gum and 85% SF 96 oil.

The organopolysiloxane resins that can be used in accordance with the disclosure may be crosslinked siloxane systems containing the following units:

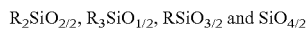

wherein R represents a hydrocarbon-based group containing 1 to 16 carbon atoms. According to at least one embodiment, R denotes a $C_1$-$C_4$ lower alkyl radical, such as methyl.

Among these resins, exemplary mention may be made of the product sold under the name Dow Corning 593 or those sold under the names SILICONE FLUID SS 4230 and SS 4267 by the company General Electric, which are silicones of dimethyl/trimethyl siloxane structure.

Exemplary mention may also be made of the trimethyl siloxysilicate type resins sold in particular under the names X22-4914, X21-5034 and X21-5037 by the company Shin-Etsu.

The organomodified silicones that can be used in accordance with the disclosure include but are not limited to silicones as defined above and comprising in their structure at least one organofunctional groups attached via a hydrocarbon-based radical.

Besides the silicones described above, the organomodified silicones may be polydiarylsiloxanes, for example, polydiphenylsiloxanes, and polyalkylarylsiloxanes functionalized with the organofunctional groups mentioned previously.

The polyalkylarylsiloxanes may be chosen, for example, from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Examples of the polyalkylarylsiloxanes may include the products sold under the following names:
  the SILBIONE® oils of the 70 641 series from Rhodia;
  the oils of the RHODORSIL® 70 633 and 763 series from Rhodia;
  the oil Dow Corning 556 Cosmetic Grade Fluid from Dow Corning;
  the silicones of the PK series from Bayer, such as the product PK20;
  the silicones of the PN and PH series from Bayer, such as the products PN1000 and PH1000;
  certain oils of the SF series from General Electric, such as SF 1023, SF 1154, SF 1250 and SF 1265.

Among the organomodified silicones, exemplary mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;
  substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, $C_1$-$C_4$ aminoalkyl groups;
  alkoxylated groups such as the product sold under the name Silicone Copolymer F-755 by SWS Silicones, and ABIL WAX® 2428, 2434 and 2440 by the company Goldschmidt.

According to at least one embodiment, the at least one fatty substance is neither oxyalkylenated nor glycerolated.

According to at least one embodiment, the at least one fatty substance is chosen from compounds that are liquid or pasty at room temperature and at atmospheric pressure.

According to at least one embodiment, the at least one fatty substance is a compound that is liquid at a temperature of 25° C. and at atmospheric pressure.

According to at least one embodiment, the fatty substance may be chosen from C6-C16 lower alkanes, fatty alcohols, fatty acid esters, fatty alcohol esters, nonsilicone oils of animal origin containing more than 16 carbon atoms, or of plant or synthetic origin, and silicones.

According to at least one embodiment, the at least one fatty substance may be chosen from liquid petroleum jelly, polybutenes, liquid esters of fatty acids or of fatty alcohols, and mixtures thereof. According to at least one embodiment, the at least one fatty substance of the composition according to the disclosure may be nonsilicone.

According to at least one embodiment, the at least one fatty substance may be chosen from alkanes, hydrocarbons, and silicones.

The composition according to the disclosure comprises at least one fatty substance, wherein the at least one fatty substance may be present in an amount greater than or equal to 25% by weight relative to the total weight of the composition. For example, the at least one fatty substance may be present in an amount ranging from 25% to 80%, such as from 25% to 65%, or from 30% to 55%, relative to the total weight of the composition.

The composition according to the disclosure comprises at least one oxidation base chosen from diaminopyrazolones and acid-addition salts thereof.

The term "diaminopyrazolones" refers to compounds comprising in their molecular structure the following sub-structure:

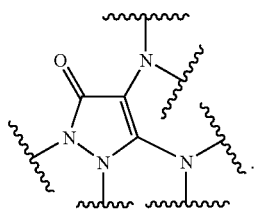

The diaminopyrazolones may be 4,5-diaminopyrazol-3-one or 2,3-aminopyrazol-1-one derivatives.

According to at least one embodiment, the oxidation base may be chosen from those of formula (I) and the acid-addition salts thereof:

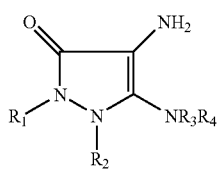

(I)

wherein: $R_1$, $R_2$, $R_3$ and $R_4$, which may be identical or different, may be independently chosen from:
a hydrogen atom;
a linear or branched $C_1$-$C_{10}$, for example, $C_1$-$C_6$, alkyl group optionally substituted with at least one group chosen from $OR_5$, $NR_6R_7$, carboxyl, sulfonic groups, carboxamido $CONR_6R_7$, sulfonamido $SO_2NR_6R_7$, aliphatic heterocycles, such as piperidine, and aryls optionally substituted with at least one group chosen from $C_1$-$C_4$ alkyl, hydroxyl, $C_1$-$C_2$ alkoxy, amino and (di)($C_1$-$C_2$)alkylamino groups;
an aryl group optionally substituted with at least one group chosen from $C_1$-$C_4$ alkyl, hydroxyl, $C_1$-$C_2$ alkoxy, amino and (di)($C_1$-$C_2$)alkylamino groups; and
a 5- or 6-membered heteroaryl group, optionally substituted with at least one group chosen from $C_1$-$C_4$ alkyl and $C_1$-$C_2$ alkoxy groups;
$R_5$, $R_6$ and $R_7$, which may be identical or different, may be independently chosen from:
a hydrogen atom;
a linear or branched $C_1$-$C_4$, for example, $C_1$-$C_2$, alkyl group optionally substituted with at least one group chosen from hydroxyl, $C_1$-$C_2$ alkoxy, carboxamido $CONR_8R_9$, sulfonyl $SO_2R_8$, and aryl groups optionally substituted with a $C_1$-$C_4$ alkyl, hydroxyl, $C_1$-$C_2$ alkoxy, amino or (di)($C_1$-$C_2$)alkylamino group;
an aryl group optionally substituted with at least one group chosen from $C_1$-$C_4$ alkyl, hydroxyl, $C_1$-$C_2$ alkoxy, amino and (di)($C_1$-$C_2$)alkylamino groups;
a carboxamido group $CONR_8R_9$; and
a sulfonyl group $SO_2R_8$;
$R_8$ and $R_9$, which may be identical or different, may independently chosen from a hydrogen atom, and a linear or branched $C_1$-$C_4$ alkyl group, optionally substituted with at least one group chosen from hydroxyl and $C_1$-$C_2$ alkoxy groups; in addition, $R_1$ and $R_2$, and/or $R_3$ and $R_4$, independently, may combine to form, together with the nitrogen atoms) to which they are attached, a saturated or unsaturated 5- to 7-membered heterocycle, optionally substituted or N-substituted with at least one group chosen from halogen, amino, (di)($C_1$-$C_4$)alkylamino, (di)hydroxy($C_1$-$C_2$)alkylamino, hydroxyl, carboxyl, carboxamido, (di)($C_1$-$C_2$)alkylcarboxamido, $C_1$-$C_2$ alkoxy, and $C_1$-$C_4$ alkyl groups optionally substituted with at least one group chosen from hydroxyl, amino, (di)alkylamino, alkoxy, carboxyl and sulfonyl groups; wherein said heterocycles independently formed by $R_1$ and $R_2$, and/or $R_3$ and $R_4$, with the nitrogen atoms to which they are attached, may be identical or different, and the chain members forming said heterocycles may be chosen, for example, from carbon, nitrogen and oxygen.

According to at least one embodiment, $R_1$ and $R_2$, which may be identical or different, may be independently chosen from:
a $C_1$-$C_6$ alkyl group optionally substituted with at least one group chosen from hydroxyl, $C_1$-$C_2$ alkoxy, amino and (di)($C_1$-$C_2$)alkylamino groups; and
a phenyl, methoxyphenyl, ethoxyphenyl or benzyl group.

According to at least one embodiment, $R_1$ and $R_2$, which may be identical or different, may be chosen, independently of each other, from methyl, ethyl, 2-hydroxyethyl, 3-hydroxypropyl, 2-hydroxypropyl, and phenyl groups.

According to at least one embodiment, $R_1$ and $R_2$ may form, together with the nitrogen atoms to which they are attached, a saturated or unsaturated 5- or 6-membered ring, optionally substituted with at least one group chosen from halogen, amino, (di)(C1-C4)alkylamino, (di)hydroxy(C1-C2)alkylamino, hydroxyl, carboxyl, carboxamido, (di)(C1-C2)alkylcarboxamido, C1-C2 alkoxy, and C1-C4 alkyl groups optionally substituted with at least one group chosen from hydroxyl, amino, (di)alkylamino, alkoxy, carboxyl, and sulfonyl groups.

According to at least one embodiment, $R_1$ and $R_2$ may form, together with the nitrogen atoms to which they are attached, a pyrazolidine or pyridazolidine ring, optionally substituted with at least one group chosen from C1-C4 alkyl, hydroxyl, C1-C2 alkoxy, carboxyl, carboxamido, amino and (di)($C_1$-$C_2$)alkylamino groups.

According to at least one embodiment, $R_1$ and $R_2$ may form, together with the nitrogen atoms to which they are attached, a pyrazolidine or pyridazolidine ring, optionally substituted with at least one group chosen from C1-C4 alkyl, hydroxyl, (C1-C2 )alkoxy, carboxyl, carboxamido, amino, and (di)(C1-C2 )alkylamino groups.

According to at least one embodiment, $R_1$ and $R_2$ may form, together with the nitrogen atoms to which they are attached, a pyrazolidine, pyridazoline or pyridazolidine ring.

According to at least one embodiment, $R_3$ and $R_4$, which may be identical or different, may be independently chosen from a hydrogen atom; a linear or branched C1-C6 alkyl group optionally substituted with at least one group chosen from hydroxyl, C1-C2 alkoxy, amino, and (di)(C1-C2 )alkylamino groups, aliphatic heterocycles such as piperidine; and a phenyl group optionally substituted with at least one group chosen from hydroxyl, amino, and C1-C2 alkoxy groups.

According to at least one embodiment, $R_3$ and $R_4$, which may be identical or different, may be independently chosen from a hydrogen atom, methyl, ethyl, isopropyl, 2-hydroxyethyl, 3-hydroxypropyl, 2-hydroxypropyl, 2-carboxyethyl, 2-dimethylaminoethyl, pyrrolidin-1-yl, 3-hydroxypyrrolidin-1-yl, 4-piperidin-1-yl, 4-methylpiperidin-1-yl and 3-dimethylaminopiperidin-1-yl groups.

According to at least one embodiment, $R_3$ and $R_4$ may be a hydrogen atom.

According to another embodiment, $R_3$ and $R_4$ may form, together with the nitrogen atom to which they are attached, a 5- to 7-membered ring chosen from pyrrolidine, piperidine, homopiperidine, piperazine and homopiperazine heterocycles; said ring possibly being substituted or N-substituted with at least one group chosen from hydroxyl, amino, (di)(C1-C2)alkylamino, (di)hydroxy(C1-C2)alkylamino, carboxyl, carboxamido, and (di)(C1-C 2)alkylcarboxamido groups, and C1-C4 alkyl groups optionally substituted with at least one groups chosen from hydroxyl, amino, and C1-C2 (di)alkylamino groups.

According to at least one embodiment, $R_3$ and $R_4$ may form, together with the nitrogen atom to which they are attached, a 5- to 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-amino-pyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 2-hydroxypiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methyl-homopiperazine and N-(2-hydroxyethyl) homopiperazine.

According to at least one embodiment, $R_3$ and $R_4$ form, together with the nitrogen atom to which they are attached, a 5- to 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, 1,4-diazepane, N-methylhomopiperazine and N-β-hydroxyethyl-homopiperazine.

According to at least one embodiment, $R_3$ and $R_4$ may form, together with the nitrogen atom to which they are attached, a 5-membered ring such as pyrrolidine, 3-hydroxypyrrolidine, 3-aminopyrrolidine or 3-dimethylaminopyrrolidine.

The compounds of formula (I) may be optionally salified with strong mineral acids, for instance HCl, HBr, HI, $H_2SO_4$ or $H_3PO_4$, or organic acids, for instance acetic acid, lactic acid, tartaric acid, citric acid or succinic acid, benzenesulfonic acid, para-toluenesulfonic acid, formic acid or methanesulfonic acid.

They may also be in the form of solvates, for example a hydrate or a solvate of a linear or branched alcohol such as ethanol or isopropanol.

Examples of compounds of formula (I) include the compounds presented below, or the acid-addition salts thereof:
4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one,
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperid-1-yl)-1,2-dimethyl-1,2-dihydropyrazol-3-one;
4,5-diamino-1,2-bis(2-hydroxyethyl)-1,2-dihydropyrazol-3-one;
4-amino-5-methylamino-1,2-bis(2-hydroxyethyl)-1,2-dihydropyrazol-3-one;
4-amino-5-dimethylamino-1,2-bis(2-hydroxyethyl)-1,2-dihydropyrazol-3-one;
4-amino-5-(2-hydroxyethyl)amino-1,2-bis(2-hydroxyethyl)-1,2-dihydropyrazol-3-one;
4-amino-5-(pyrrolidin-1-yl)-1,2-di(2-hydroxyethyl)-1,2-dihydropyrazol-3-one,
4-amino-5-(piperid-1-yl)-1,2-di(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperid-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6,6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;

4-amino-5-(2-dimethylaminoethylamino)-1,2-diethyl-1,2-dihydropyrazol-3-one;

4-amino-5-[bis(2-hydroxyethyl)amino]-1,2-diethyl-1,2-dihydropyrazol-3-one;

4-amino-1,2-diethyl-5-(3-imidazol-1-ylpropylamino)-1,2-dihydropyrazol-3-one;

4-amino-5-(3-dimethylaminopyrrolidin-1-yl)-1,2-diethyl-1,2-dihydropyrazol-3-one;

4-amino-1,2-diethyl-5-(4-methylpiperazin-1-yl)pyrazolidin-3-one; some of which are given below to illustrate the names with chemical structures:

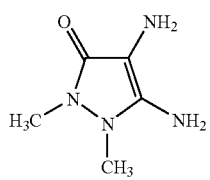
4,5-diamino-1,2-dimethyl-1,2-dihydropyrazol-3-one

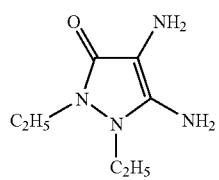
4,5-diamino-1,2-diethyl-1,2-dihydropyrazol-3-one

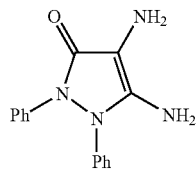
4,5-diamino-1,2-diphenyl-1,2-dihydropyrazol-3-one

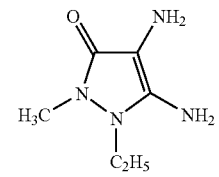
4,5-diamino-1-ethyl-2-methyl-1,2-dihydropyrazol-3-one

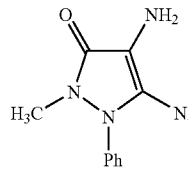
4,5-diamino-1-phenyl-2-methyl-1,2-dihydropyrazol-3-one

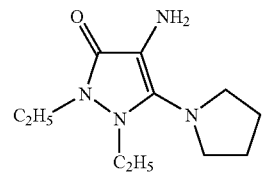
4-amino-5-(pyrrolidin-1-yl)-1,2-diethyl-1,2-dihydropyrazol-3-one

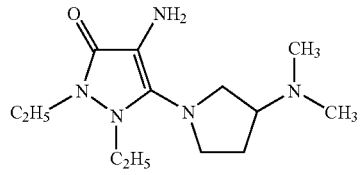
4-amino-5-(3-dimethylaminopyrrolidin-1-yl)-1,2-diethyl-1,2dihydropyrazol-3-one

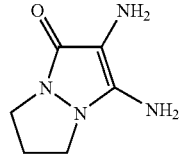
2,3-diamino-6,7-dihydro-1H,5H-pyrazolo[1,2-a]pyrazol-1-one

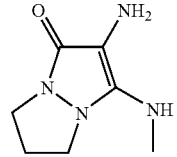
2-amino-3-methylamino-6,7-dihydro-1H,5H-pyrazolo-[1,2-a]pyrazol-1-one

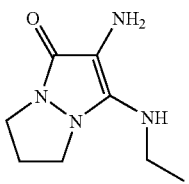
2-amino-3-ethylamino-6,7-dihydro-1H,5H-pyrazolo-[1,2-a]pyrazol-1-one

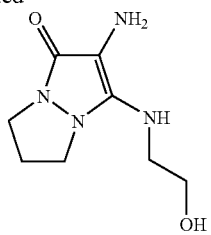
2-amino-3-(2-hydroxyethyl)-amino-6,7-dihydro-1H,5H-pyrazolo[1,2-a]pyrazol-1-one

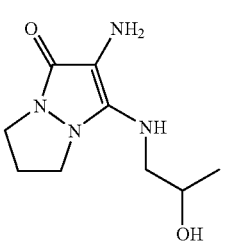
2-amino-3-(2-hydroxypropyl)-amino-6,7-dihydro-1H,5H-pyrazolo[1,2-a]pyrazol-1-one

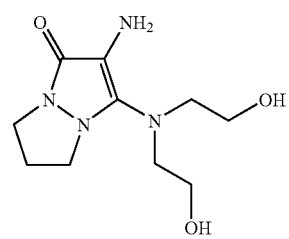
2-amino-3-bis(2-hydroxyethyl)-amino-6,7-dihydro-1H,5H-pyrazolo[1,2-a]pyrazol-1-one

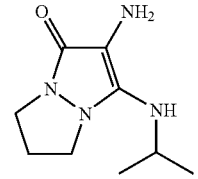
2-amino-3-isopropylamino-6,7-dihydro-1H,5H-pyrazolo-[1,2-a]pyrazol-1-one

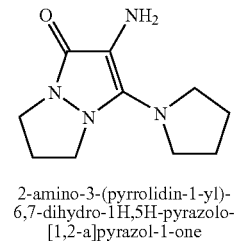
2-amino-3-(pyrrolidin-1-yl)-6,7-dihydro-1H,5H-pyrazolo-[1,2-a]pyrazol-1-one

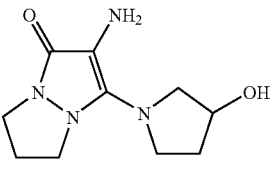
2-amino-3-(3-hydroxypyrrolidin-1-yl)-6,7-dihydro-1H,5H-pyrazolo-[1,2-a]pyrazol-1-one

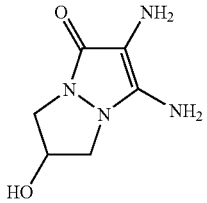
2,3-diamino-6-hydroxy-6,7-dihydro-1H,5H-pyrazolo-[1,2-a]pyrazol-1-one

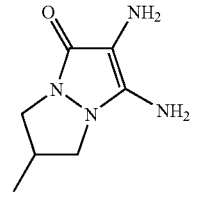
2,3-diamino-6-methyl-6,7-dihydro-1H,5H-pyrazolo-[1,2-a]pyrazol-1-one

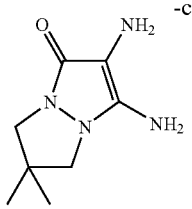

2,3-diamino-6,6-dimethyl-
6,7-dihydro-1H,5H-pyrazolo-
[1,2-a]pyrazol-1-one

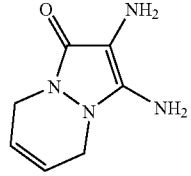

2,3-diamino-5,8-dihydro-1H,6H-
pyridazino[1,2-a]pyrazol-1-one

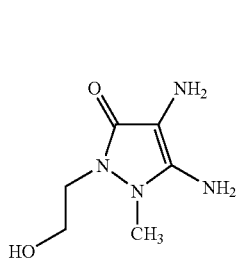

4,5-diamino-2-(2-hydroxyethyl)-1-methyl-
1,2-dihydropyrazol-3-one

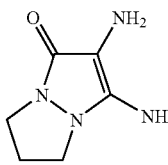

2,3-diamino-5,6,7,8-tetrahydro-
1H,6H-pyridazino[1,2-a]-
pyrazol-1-one

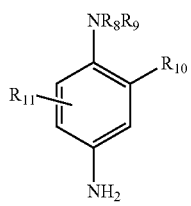

4,5-diamino-1-
(2-hydroxyethyl)-2-methyl-
1,2-dihydropyrazol-3-one

Examples of the diamino-N,N-dihydropyrazolones of formula (I), or the addition salts thereof, include the following:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-bis(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one.

According to at least one embodiment, the at least one oxidation base may be chosen from 2,3-Diamino-6,7-dihydro-1H,5H-pyrazolo[1,2-a]pyrazol-1-one and salts thereof such as 2,3-diamino-6,7-dihydro-1H,5H-pyrazolo[1,2-a]pyrazol-1-one dimethanesulfonate, of formula:

The amount of the at least one oxidation base, which may be chosen from diaminopyrazolones and acid-addition salts thereof, ranges from 0.005% to 10%, for example from 0.05% to 1.5%, by weight relative to the total weight of the composition.

In addition to the at least one oxidation base that may be chosen from diaminopyrazolones and acid-addition salts thereof, the composition may comprise at least one additional dye precursor.

The at least one additional dye precursor may be chosen from oxidation bases other than diaminopyrazolones or acid-addition salts thereof, and couplers.

The at least one additional dye precursor may be chosen from oxidation bases such as ortho- and para-phenylenediamines, double bases, ortho- and para-aminophenols and heterocyclic bases, and also the acid-addition salts of these compounds.

These oxidation bases may for example, be cationic.

The para-phenylenediamines that may be used in the context of the disclosure may be chosen, for example, from the compounds of formula (II) below, and the acid-addition salts thereof:

(II)

wherein:
$R_8$ may be chosen from a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical, a $C_1$-$C_4$ alkyl radical substituted with a nitrogenous radical, a phenyl radical and a 4'-aminophenyl radical;
$R_9$ may be chosen from a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical and a $C_1$-$C_4$ alkyl radical substituted with a nitrogenous radical;
$R_8$ and $R_9$ may also form, with the nitrogen atom that they are attached to, a 5- or 6-membered nitrogenous heterocycle optionally substituted with at least one alkyl, hydroxy or ureido groups;
$R_{10}$ may be chosen from a hydrogen atom, a halogen atom such as a chlorine atom, a $C_1$-$C_4$ alkyl radical, a sulfo radical, a carboxy radical, a $C_1$-$C_4$ monohydroxyalkyl radical, a $C_1$-$C_4$ hydroxyalkoxy radical, an acetylamino($C_1$-$C_4$)alkoxy radical, a $C_1$-$C_4$ mesylaminoalkoxy radical and a carbamoylamino($C_1$-$C_4$)alkoxy radical;
$R_{11}$ may be chosen from hydrogen, halogen, and a $C_1$-$C_4$ alkyl radical.

Among the nitrogenous groups of formula (II) above, exemplary mention may be made of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Examples of the para-phenylenediamines of formula (II) include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and the acid-addition salts thereof.

According to at least one embodiment, the para-phenylenediamines of formula (II) above may be chosen from para-phenylenediamine, para-tolylenediamine, 2-isopropyl-para-phenylenediamine, 2-β-hydroxyethyl-para-phenylenediamine, 2,6-dimethyl-para-phenylenediamine, 2,6-diethyl-para-phenylenediamine, 2,3-dimethyl-para-phenylenediamine, 2-chloro-para-phenylenediamine and N,N-bis(β-hydroxyethyl)-para-phenylenediamine, and the acid-addition salts thereof.

According to at least one embodiment, the para-phenylenediamines of formula (II) above may be chosen from para-Phenylenediamine, para-tolylenediamine and N,N-bis-β-hydroxyethyl-para-phenylenediamine, and the acid-addition salts thereof.

According to the disclosure, the term "double bases" refers to compounds comprising at least two aromatic nuclei bearing amino and/or hydroxyl groups.

Examples of double bases include the compounds of formula (III) below, and the acid-addition salts thereof:

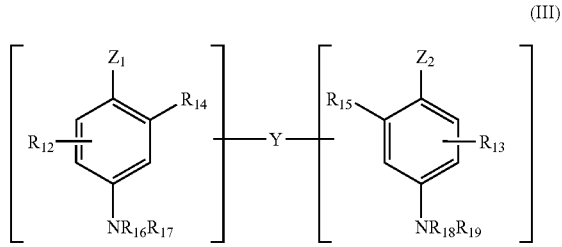

(III)

wherein:
$Z_1$ and $Z_2$, which may be identical or different, may be independently chosen from a hydroxyl or —$NH_2$ group that may be optionally substituted with a $C_1$-$C_4$ alkyl group or with a linker arm Y;
the linker arm Y may be chosen from a linear or branched alkylene chain containing from 1 to 14 carbon atoms, which may be interrupted by or terminated with at least one nitrogenous groups and/or at least one heteroatom such as oxygen, sulfur or nitrogen atoms, and optionally substituted with at least one hydroxyl or $C_1$-$C_6$ alkoxy group;
$R_{12}$ and $R_{13}$ may be chosen from hydrogen, halogen, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical and a linker arm Y;
$R_{14}$, $R_{15}$, $R_{16}$, $R_{17}$, $R_{18}$ and $R_{19}$, which may be identical or different, may be independently chosen from hydrogen, a linker arm Y and a $C_1$-$C_4$ alkyl radical;
wherein the compounds of formula (III) may contain only one linker arm Y per molecule.

Examples of the nitrogenous groups of formula (III) above include amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Examples of the double bases of formula (III) above include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid-addition salts thereof.

According to at least one embodiment, the double bases of formula (III) may be chosen from N,N'-bis(β-hydroxyethyl)-N,N'-bis(4'-aminophenyl)-1,3-diaminopropanol and 1,8-bis(2,5-diaminophenoxy)-3,5-dioxaoctane, and the acid addition salts thereof.

The para-aminophenols that may be used in the context of the disclosure may be chosen, for example, from the compounds of formula (IV) below, and the acid-addition salts thereof:

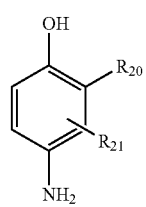

(IV)

wherein:
$R_{20}$ may be chosen from a hydrogen atom, a halogen atom such as fluorine, a $C_1$-$C_4$ alkyl group, a $C_1$-$C_4$ monohydroxyalkyl group, a ($C_1$-$C_4$)alkoxy($C_1$-$C_4$)alkyl group, a $C_1$-$C_4$ aminoalkyl group and a hydroxy($C_1$-$C_4$)alkylamino($C_1$-$C_4$)alkyl group,
$R_{21}$ may be chosen from a hydrogen atom, a halogen atom such as fluorine, a $C_1$-$C_4$-alkyl group, a $C_1$-$C_4$ monohydroxyalkyl group, a $C_2$-$C_4$ polyhydroxyalkyl group, a $C_1$-$C_4$ aminoalkyl group, a $C_1$-$C_4$ cyanoalkyl group and a ($C_1$-$C_4$)alkoxy($C_1$-$C_4$)alkyl group.

Examples of the para-aminophenols of formula (IV) include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the acid-addition salts thereof.

According to at least one embodiment, the at least one additional dye precursor may be chosen from para-Aminophenol and 4-amino-3-methylphenol.

The ortho-aminophenols that may be used as oxidation bases in the context of the present disclosure may be chosen, for example, from 2-aminophenol, 2-amino-1-hydroxy-5-methylbenzene, 2-amino-1-hydroxy-6-methylbenzene and 5-acetamido-2-aminophenol, and the acid addition salts thereof.

Examples of the heterocyclic bases which can be used as oxidation bases in the dye compositions in accordance with the disclosure include pyridine derivatives, pyrimidine derivatives, pyrazole derivatives, and the acid-addition salts thereof.

Examples of the pyridine derivatives include the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid-addition salts thereof.

Examples of the pyrimidine derivatives also include the compounds described, for example, in German patent DE 2 359 399 or Japanese patents JP 88-169 571 and JP 91-10659 or patent application WO 96/15765, such as 2,4,5,6-tetramino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylaminopyrazolo[1,5-a]pyrimidine and the addition salts thereof and the tautomeric forms thereof, when a tautomeric equilibrium exists, and the acid-addition salts thereof.

Examples of the pyrazole derivatives include the compounds described in patents DE 3 843 892, DE 4 133 957 and patent applications WO 94/08969, WO 94/08970, FR-A-2 733 749 and DE 195 43 988, such as 4,5-diaminopyrazoles, for instance 4,5-diamino-1-methylpyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-β-hydroxyethyl)-3-methylpyrazole, 4,5-diamino-1-β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4-diaminopyrazole, 4-amino-1,3-dimethyl-5-hydrazinopyrazole, 3,4,5-triaminopyrazoles, for instance 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid-addition salts thereof.

According to at least one embodiment, 4,5-diaminopyrazoles such as 4,5-diamino-1-(β-hydroxyethyl)pyrazole and/or a salt thereof may be used.

Examples of cationic oxidation bases that may be used in the compositions according to the disclosure include the following compounds: para-phenylenediamines as described, for example, in patent applications FR-A-2 766 177 and FR-A-2 766 178, para-aminophenols as described, for example, in patent applications FR-A-2 766 177 and FR-A-2 766 178, ortho-phenylenediamines as described, for example, in patent applications FR-A-2 782 718, FR-A-2 782 716 and FR-A-2 782 719, ortho-aminophenols or cationic double bases such as derivatives of bis(aminophenyl)alkylenediamine type described in patent application FR-A-2 766 179, and also cationic heterocyclic bases, which has at least one quaternary nitrogen atom.

According to at least one embodiment, the cationic oxidation bases may be chosen from cationic para-phenylenediamines.

According to at least one embodiment, cationic oxidation bases of para-phenylenediamine structure can be used, wherein at least one of the amine function is a tertiary amine bearing a pyrrolidine nucleus, the molecule comprising at least one quaternized nitrogen atom. Such bases are described, for example, in document European Patent Application Publication No. 1 348 695.

According to at least one embodiment, the composition according to the present disclosure comprises at least one oxidation base present in a total amount ranging from 0.0005% to 12% by weight relative to the total weight of the composition. For example, the total amount of the at least one oxidation base may range from 0.005% to 8% by weight, such as from 0.05% to 5% by weight, relative to the total weight of said composition.

Examples of the couplers that may be used in the composition according to the disclosure include those conventionally used in oxidation dye compositions, i.e. meta-aminophenols, meta-phenylenediamines and meta-diphenols, naphthols and heterocyclic couplers such as, indole derivatives, indoline derivatives, sesamol and derivatives, pyridine derivatives, pyrazolotriazole derivatives, pyrazolones, indazoles, benzimidazoles, benzothiazoles, benzoxazoles, 1,3-benzodioxoles and quinolines, and the acid-addition salts thereof.

The couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the acid-addition salts thereof.

The composition according to the disclosure may comprise at least one coupler present in a total amount ranging from 0.0001% to 15% by weight relative to the total weight of the composition. For example, the total amount of the at least one coupler may range from 0.001% to 10% by weight, for example, from 0.01% to 8% by weight, relative to the total weight of the composition.

The oxidation bases and couplers may be present in the compositions of the disclosure in the form of addition salts, for example, in the form of acid-addition salts.

The acid-addition salts may be chosen, for example, from hydrochlorides, hydrobromides, sulfates, citrates, succinates, tartrates, lactate, acetates, alkyl sulfates and alkyl sulfonates.

When the oxidation bases or the couplers contain at least one carboxylic or sulfonic acid functions, base-addition salts may be envisioned. Examples of the base-addition salts include those obtained with sodium hydroxide, potassium hydroxide, ammonia or amines.

According to at least one embodiment, the composition comprises at least one additional oxidation base and at least one coupler.

According to at least one embodiment, the additional oxidation base may be chosen from para-aminophenols, heterocyclic bases, and the acid-addition salts thereof.

The composition in accordance with the present disclosure may comprise at least one oxidizing agent.

The at least one oxidizing agent may be chosen, for example, from peroxides such as hydrogen peroxide and urea peroxide, alkali metal bromates or ferricyanides, and persalts such as perborates, percarbonates and persulfates. At least one redox enzyme such as laccases, peroxidases and 2-electron oxidoreductases (such as uricase), optionally in the presence of the respective donor or cofactor thereof, may also be used as an oxidizing agent.

According to at least one embodiment, the at least one oxidizing agent may be hydrogen peroxide. The at least one oxidizing agent may be used in the form of an aqueous hydrogen peroxide solution whose strength may range, for example, from about 1 to 40 volumes, such as from about 5 to 40 volumes.

The concentration of the at least one oxidizing agents may range from 0.1% to 20%, for example, from 0.5% to 10%, of the total weight of the composition.

The composition of the disclosure can comprise at least one alkaline agent. The at least one alkaline agent may be chosen from mineral bases, organic amines and organic amine salts, alone or as a mixture. According to at least one embodiment, the composition may contain at least one alkaline agent.

Examples of organic amines include organic amines with a pKb at 25° C. of less than 12, for example, less than 10, such as less than 6. It should be noted that the pKb corresponds to the function of the highest basicity.

The organic amine may comprise one or two primary, secondary or tertiary amine functions, and at least one linear or branched C1-8 alkyl group bearing at least one hydroxyl radical.

According to at least one embodiment, organic amines may be chosen from alkanolamines such as mono-, di- or trialkanolamines, comprising one to three identical or different C1-C4 hydroxyalkyl radicals.

Examples of alkanolamines include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

The organic amines may also be chosen from those of the following formula:

$$\begin{array}{c} R_x \\ \phantom{R}\diagdown \\ \phantom{RR}N-W-N \\ \phantom{R}\diagup \phantom{RRRRR}\diagdown \\ R_y \phantom{RRRRRRRR} R_t \end{array} \begin{array}{c} R_z \\ \diagup \\ \phantom{R} \\ \phantom{R} \end{array}$$

wherein W may be a C1-C6 alkylene residue optionally substituted with a hydroxyl group or a C1-C6 alkyl radical; Rx, Ry, Rz and Rt, which may be identical or different, may be independently chosen from hydrogen, and C1-C6 alkyl, C1-C6 hydroxyalkyl or C1-C6 aminoalkyl radicals.

Examples of such amines include 1,3-diaminopropane, 1,3-diamino-2-propanol, spermine and spermidine.

According to alt least one embodiment, the at least one organic amine may be chosen from amino acids.

Examples of the amino acids that may be used include those of natural or synthetic origin, in L, D or racemic form, and comprise at least one acid function chosen, for example, from carboxylic acid, sulfonic acid, phosphonic acid and phosphoric acid functions. The amino acids may be in their neutral or ionic form.

For example, the amino acids may be basic amino acids comprising an additional amine function optionally included in a ring or in a ureido function.

Such basic amino acids may be, for example, chosen from those corresponding to formula (I) below:

$$R-CH_2-CH\begin{array}{c} NH_2 \\ \diagup \\ \diagdown \\ CO_2H \end{array} \quad (I)$$

wherein R may be chosen from:

—imidazolylmethyl (histidine ring); —(CH$_2$)$_3$NH$_2$; —(CH$_2$)$_2$NH$_2$;

—(CH$_2$)$_2$NHCONH$_2$; and

—(CH$_2$)$_2$NH—C(=NH)—NH$_2$.

The compounds corresponding to formula (I) may be histidine, lysine, arginine, ornithine and citrulline.

Examples of amino acids that may be used in the present disclosure include aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine and valine.

According to at least one embodiment, the at least one organic amine may be chosen from basic amino acids, for example, arginine, lysine and histidine.

According to at least one embodiment, the at least one organic amine may be chosen from organic amines of heterocyclic type, for example, histidine, pyridine, piperidine, imidazole, 1,2,4-triazole, tetrazole and benzimidazole.

According to at least one embodiment, the at least one organic amine may be chosen from amino acid dipeptides, for example, carnosine, anserine and baleine.

According to at least one embodiment, the at least one organic amine may be chosen from compounds comprising a guanidine function. Examples of amines of this type include arginine, creatine, creatinine, 1,1-dimethylguanidine, 1,1-diethylguanidine, glyco-cyamine, metformin, agmatine, N-amidinoalanine, 3-guanidinopropionic acid, 4-guanidinobutyric acid and 2-([amino(imino)methyl]amino)ethane-1-sulfonic acid.

For example, the at least one organic amine may be an alkanolamine. According to at least one embodiment, the at least one organic amine may be chosen from 2-amino-2-methyl-1-propanol and monoethanolamine, or mixtures thereof. According to at least one embodiment, the organic amine is monoethanolamine.

The at least one alkaline agent may be an organic amine in salt form. The term "organic amine salt" means organic or mineral salts of an organic amine as described above.

For example, the organic salts may be chosen from the salts of organic acids, such as citrates, lactates, glycolates, gluconates, acetates, propionates, fumarates, oxalates and tartrates.

For example, the mineral salts may be chosen from hydrohalides (for example hydrochlorides), carbonates, hydrogen carbonates, sulfates, hydrogen phosphates and phosphates.

The term "mineral compound" means any compound bearing in its structure at least one element from columns 1 to 13 of the Periodic Table of the Elements other than hydrogen, not simultaneously comprising carbon and hydrogen atoms.

According to at least one embodiment, the mineral base may contain one or more elements from columns 1 and 2 of the Periodic table of the Elements other than hydrogen.

According to at least one embodiment, the mineral base has the following structure:

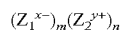

wherein
$Z_2$ denotes a metal from columns 1 to 13, for example, column 1 or 2 of the Periodic Table of the Elements, such as sodium or potassium;
$Z_1^{x-}$ denotes an anion chosen from the ions $CO_3^{2-}$, $OH_-$, $HCO_3^{2-}$, $SiO_3^{2-}$, $HPO_4^{2-}$, $PO_4^{3-}$ and $B_4O_7^{2-}$, and according to at least one embodiment, $Z_1^{x-}$ denotes an anion chosen from the ions $CO_3^{2-}$, $OH^-$ and $SiO_3^{2-}$;
x denotes 1, 2 or 3;
y denotes 1, 2, 3 or 4;
m and n denote, independently of each other, 1, 2, 3 or 4;
with (n)(y)=(m)(x)

According to at least one embodiment, the mineral base corresponds to the following formula $(Z_1^{x-})_m(Z_2^{y+})_n$ wherein $Z_2$ denotes a metal chosen from columns 1 and 2 of the Periodic Table of the Elements; $Z_1^{x-}$ denotes an anion chosen from the ions $CO_3^{2-}$, $OH^-$ and $SiO_3^{2-}$, x is 1, y denotes 1 or 2, and m and n denote, independently of each other, 1 or 2 with (n)(y)=(m)(x).

Example of the mineral bases include sodium bicarbonate, potassium carbonate, sodium hydroxide, potassium hydroxide, sodium metasilicates and potassium metasilicate.

The at least one alkaline agent may also be chosen from ammonium salts.

The ammonium salts that may be used according to the present disclosure may be chosen from ammonium salts ($NH_4^+$).

The ammonium salts may also be chosen from the following acid salts: acetate, carbonate, bicarbonate, chloride, citrate, nitrate, nitrite, phosphate, and sulfate. According to at least one embodiment, the salt is chosen from carbonate salts, such as ammonium carbonate.

According to at least one embodiment, the composition comprises at least one alkaline agent chosen from organic amines, for example, alkanolamines. When the composition contain more than one alkaline agents, such as an alkanolamine and ammonium hydroxides or their salts, the amount of organic amine(s) are, according to at least one embodiment, higher than the amount of ammonia.

The amount of the at least one alkaline agent in the composition of the disclosure may, for example, range from 0.01% to 30%, for example, from 0.1% to 20%, by weight of the total weight of the composition.

The dye composition in accordance with the disclosure may also comprise at least one direct dye, which may be chosen, for example, from nitrobenzene dyes, azo direct dyes and methine direct dyes, and the addition salts thereof. These direct dyes may be of nonionic, anionic or cationic nature.

The composition may also comprise other compounds constituting the dyeing medium. The dyeing medium may comprise water or a mixture of water and at least one cosmetically acceptable organic solvent, which may be water-soluble.

Examples of organic solvents include alcohols such as ethyl alcohol, isopropyl alcohol, benzyl alcohol and phenylethyl alcohol, or glycols or glycol ethers, for instance ethylene glycol monomethyl, monoethyl or monobutyl ether, propylene glycol or ethers thereof, for instance propylene glycol monomethyl ether, butylene glycol, hexylene glycol, dipropylene glycol, and also diethylene glycol alkyl ethers, for instance diethylene glycol monoethyl ether or monobutyl ether. The solvents may be present in concentrations ranging from about 0.01% to 35% by weight, for example, from about 0.1% to 25% by weight, relative to the total weight of the composition.

According to at least one embodiment, the composition of the disclosure may comprise water. For example, the water may be present in an amount ranging from 10% to 70%, for example, from 20% to 55%, by weight of the total weight of the composition.

The composition in accordance with the disclosure may also comprise at least one adjuvants conventionally used in hair dye compositions.

The term "adjuvant" means an additive other than the above-mentioned compounds.

Examples of adjuvants include anionic, cationic, nonionic, amphoteric or zwitterionic surfactants or mixtures thereof; anionic, cationic, nonionic, amphoteric or zwitterionic polymers, mineral or organic thickeners, for example, anionic, cationic, nonionic and amphoteric polymeric associative thickeners, other than the associative celluloses according to the disclosure; antioxidants or reducing agents; penetrants; sequestrants; fragrances; buffers; dispersants; conditioning agents, for instance volatile or nonvolatile, modified or unmodified silicones; film-forming agents; ceramides; preserving agents; opacifiers; and antistatic agents.

The above adjuvants may be each present in an amount ranging from 0.01% to 20% by weight relative to the weight of the dye composition.

According to at least one embodiment, the composition of the disclosure may comprise at least one surfactant.

For example, the at least one surfactant may be chosen from nonionic surfactants and anionic surfactants.

The anionic surfactants may be, for example, chosen from the salts (for instance alkali metal salts, such as sodium salts, ammonium salts, amine salts, amino alcohol salts or alkaline-earth metal salts such as magnesium salts) of the following compounds:
alkyl sulfates, alkyl ether sulfates, alkylamido ether sulfates, alkylaryl polyether sulfates, monoglyceride sulfates;
alkylsulfonates, alkylamidesulfonates, alkylarylsulfonates, α-olefin sulfonates, paraffin sulfonates;
alkyl phosphates, alkyl ether phosphates;

alkylsulfosuccinates, alkyl ether sulfosuccinates, alkylamidesulfosuccinates; alkylsulfosuccinates;
alkylsulfoacetates;
acylsarcosinates; acylisethionates and N-acyltaurates;
salts of fatty acids such as oleic acid, ricinoleic acid, palmitic acid or stearic acid, coconut oil acid or hydrogenated coconut oil acid;
alkyl-D-galactoside uronic acid salts;
acyllactylates;
salts of polyoxyalkylenated alkyl ether carboxylic acids, of polyoxyalkylenated alkylaryl ether carboxylic acids or of polyoxyalkylenated alkylamido ether carboxylic acids, for example, those containing from 2 to 50 ethylene oxide groups;
and mixtures thereof.

It should be noted that the alkyl or acyl radical of these various compounds may contain from 6 to 24 carbon atoms, for example, from 8 to 24 carbon atoms, and the aryl radical, for example, may be a phenyl or benzyl group.

The nonionic surfactants may be, for example, chosen from monooxyalkylenated or polyoxyalkylenated, monoglycerolated or polyglycerolated nonionic surfactants. The oxyalkylene units are for example, oxyethylene or oxypropylene units, or a combination thereof. According to at least one embodiment, the oxyalkylene units may be oxyethylene units.

Examples of oxyalkylenated nonionic surfactants include:
oxyalkylenated ($C_8$-$C_{24}$)alkylphenols,
saturated or unsaturated, linear or branched, oxyalkylenated $C_8$-$C_{30}$ alcohols,
saturated or unsaturated, linear or branched, oxyalkylenated $C_8$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils, and
condensates of ethylene oxide and/or of propylene oxide, inter alia, alone or as mixtures.

The surfactants may contain a number of moles of ethylene oxide and/or of propylene oxide ranging from 1 to 50, for example, from 2 to 30. According to at least one embodiment, the nonionic surfactants do not comprise any oxypropylene units.

According to at least one embodiment, the oxyalkylenated nonionic surfactants are chosen from oxyethylenated C8-C30 alcohols, for example, oxyethylenated C18-C30 amines.

According to at least one embodiment, monoglycerolated or polyglycerolated nonionic surfactants, for example, monoglycerolated or polyglycerolated C8-C40 alcohols may be used.

For example, the monoglycerolated or polyglycerolated C8-C40 alcohols may be of the following formula:

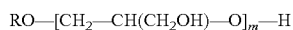

$$RO-[CH_2-CH(CH_2OH)-O]_m-H$$

wherein R may be a linear or branched $C_8$-$C_{40}$, for example, $C_8$-$C_{30}$ alkyl or alkenyl radical, and m may be a number ranging from 1 to 30, for example, from 1 to 10.

Examples of the monoglycerolated or polyglycerolated C8-C40 alcohols include lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may be a mixture of alcohols in the same way that the value of m represents a statistical value, which means that, in a commercial product, several species of polyglycerolated fatty alcohol may coexist in the form of a mixture.

According to at least one embodiment, the monoglycerolated or polyglycerolated alcohols may be chosen from the C8/C10 alcohols containing 1 mol of glycerol, the C10/C12 alcohols containing 1 mol of glycerol and the C12 alcohols containing 1.5 mol of glycerol.

According to at least one embodiment, the surfactant present in the composition may be a nonionic surfactant.

The surfactant may be present in the composition in an amount ranging from 0.1% to 50% by weight, for example, from 0.5% to 30% by weight, relative to the weight of the composition.

Needless to say, a person skilled in the art would take care to select the optional adjuvant(s) mentioned above, such that the advantageous properties intrinsically associated with the compositions according to the disclosure are not, or are not substantially, adversely affected by the envisioned addition(s).

The pH of the composition in accordance with the disclosure may generally range from 3 to 12 approximately, for example, from 5 to 11 approximately, such as from 7 to 11. It may be adjusted to the desired value by means of acidifying or basifying agents usually used in the dyeing of keratin fibers or alternatively using standard buffer systems.

The alkaline agents may be, for example, those described previously.

Among the acidifying agents, examples that may be mentioned include mineral or organic acids, for instance hydrochloric acid, orthophosphoric acid, carboxylic acids, for instance tartaric acid, citric acid or lactic acid, or sulfonic acids.

The dye composition according to the disclosure may be in various forms, such as in the form of liquids, creams or gels, or in any other form that is suitable for dyeing keratin fibers, such as human hair.

One aspect of the present disclosure is a process for dyeing keratin fibers, comprising: providing a composition comprising: A) at least one fatty substance, wherein the at least one fatty substance is present in an amount greater than or equal to 25% by weight relative to the total weight of the composition; B) at least one oxidation base chosen from diaminopyrazolones and acid-addition salts thereof; C) at least one additional dye precursor other than the oxidation base in B); D) at least one oxidizing agent, and optionally; E) at least one alkaline agent; and applying the composition to the keratin fibers for a time that is sufficient to develop the desired coloration. The color may be revealed at acidic, neutral or alkaline pH and the oxidizing agent may be employed just at the time of use, or it may be employed simultaneously with or sequentially to the other compounds of the composition of the disclosure.

After a leave-on time generally ranging from 1 to 60 minutes approximately, for example, 5 to 45 minutes approximately, the keratin fibers may be rinsed, optionally washed with shampoo, rinsed again and then dried.

The composition according to the disclosure may result from the mixing of at least two compositions, such as, two or three compositions, for example, including an oxidizing composition comprising at least one oxidizing agent as defined previously.

One aspect of the disclosure is also a multi-compartment device or dyeing "kit" comprising: a first compartment comprising (A) at least one fatty substance; a second compartment comprising (B) at least one oxidation base chosen from diaminopyrazolones and acid-addition salts thereof, (C) at least one additional dye precursor other than the at least one oxidation base in (B), and optionally (E) at least one alkaline agent; and a third compartment comprising (D) at least one oxidizing agent and optionally at least one fatty substance. According to at least one embodiment, the composition comprising the fatty substance(s) may be anhydrous. The term "anhydrous composition" means a cosmetic composition having a water content of less than 5% by weight, for example, less than 2% by weight, such as less than 1% by weight, relative to the weight of said composition. It should be noted that it may have bound water, such as the water of crystallization of salts, or traces of water absorbed by the starting materials used in the preparation of the compositions according to the disclosure.

According to at least one embodiment, the device of the disclosure comprises a first compartment comprising a composition comprising (A) at least one fatty substance and (D) at least one oxidizing agent; and a second compartment comprising (B) at least one oxidation base chosen from diaminopyrazolones and acid-addition salts thereof, (C) at least one additional dye precursor other than the oxidation base in (B), and optionally (E) at least one alkaline agent. This device may be equipped with a means for applying the desired mixture to the hair, such as the devices described in patent FR-A-2 586 913 in the name of the Applicant.

According to at least one embodiment, the device of the disclosure comprises a first compartment comprising a composition comprising (A) at least one fatty substance, (B) at least one oxidation base chosen from diaminopyrazolones and acid-addition salts thereof, (C) at least one additional dye precursor other than the at least one oxidation base in (B), and optionally (E) at least one alkaline agent; and a second compartment comprising (D) at least one oxidizing agent.

The examples that follow are intended to illustrate the disclosure without, however, in any way limiting its scope.

EXAMPLES

Example 1

The following compositions were prepared:

| Composition 1 | Concentration (g %) |
| --- | --- |
| Disteardimonium hectorite | 3 |
| Octyldodecanol | 11.5 |
| Glycol distearate | 8 |
| Liquid petroleum jelly | 64.5 |
| Propylene carbonate | 1 |
| Laureth-2 | 1 |
| Polysorbate 21 | 11 |

| Composition 2 | Concentration (g %) |
| --- | --- |
| Diethylenetriaminepentaacetic acid, pentasodium salt, as an aqueous 40% solution | 1 |
| Sodium metabisulfite | 0.7 |
| Monoethanolamine | 14.5 |
| 1-Methyl-2,5-diaminobenzene | 0.52 |
| para-Aminophenol | 0.725 |
| 1-Methyl-2-hydroxy-4-aminobenzene | 3.64 |
| 2,3-Diamino-6,7-dihydro-1H,5H-pyrazolo[1,2-a]pyrazol-1-one dimethanesulfonate | 5.8 |
| Natrosol 250 HHR (hydroxyethylcellulose) | 1.5 |
| Hexylene glycol | 3 |
| Dipropylene glycol | 3 |
| Ethyl alcohol | 8.25 |
| Propylene glycol | 6.2 |
| Ascorbic acid | 0.25 |
| Water | qs 100 g |

| Composition 3 | Concentration (g %) |
| --- | --- |
| Diethylenetriaminepentaacetic acid, pentasodium salt, as an aqueous 40% solution | 0.15 |
| Hydrogen peroxide as an aqueous 50% solution (200 vol. aqueous hydrogen peroxide solution) | 12 |
| Sodium stannate | 0.04 |
| Sodium pyrophosphate | 0.03 |
| Liquid petroleum jelly | 20 |
| Hexadimethrine chloride (containing 60% AM in water) | 0.25 |
| Polyquaternium-6 (containing 40% AM in water) | 0.5 |
| Glycerol | 0.5 |
| Cetylstearyl alcohol (30/70 C16/C18) | 8 |
| Oxyethylenated cetylstearyl alcohol (33 EO) | 3 |
| Protected oxyethylenated (4 EO) rapeseed acid amide at 92.3% in water | 1.3 |
| Vitamin E | 0.1 |
| Phosphoric acid | qs pH 2.2 |
| Water | qs 100 g |

The three compositions were mixed together at the time of use in the following proportions: 10 g of composition 1 with 4 g of composition 2 and 16 g of composition 3. The mixture was applied to locks of natural gray hair containing 90% gray hairs, at a rate of 10 g of mixture per 1 g of hair. After a leave-on time of 30 minutes, the hair was rinsed, washed with a standard shampoo and dried.

The hair coloration was evaluated visually.

| Example 1 | Light chestnut with a strong red-coppery tint |
| --- | --- |

Example 2

The following compositions A1 and A2 were prepared (quantity expressed in grams):

|  | A1 | A2 (inventive) |
| --- | --- | --- |
| isopropyle Myristate | 52 | 87 |
| Oleth-10 | 10 | 10 |
| Disteardimonium hectorite | 2.25 | 2.25 |
| propylene Carbonate | 0.75 | 0.75 |
| water | 35 | — |

Composition B (quantity expressed in grams):

| | |
|---|---|
| dimethanesulfonate 2,3-diamino-6,7-dihydro-1H,5H-pyrazolo[1,2-A]pyrazol-1-one | 5.017 |
| 2-méthyl 5-aminophenol | 1.7835 |
| Hydroxyethyl cellulose (Natrosol 250 HHR) | 1.5 |
| Dipropylene glycol | 3 |
| Hexylene glycol | 3 |
| Propylene glycol | 6.2 |
| Monoethanolamine | 15.04 |
| ethanol | 8.25 |
| Reducing agent, sequestring agent | qs |
| water | Qs 100 |

Composition C (quantity expressed in grams):

| | |
|---|---|
| hydrogen Peroxide | 6 |
| Cetearylic alcohol | 2.28 |
| Ceteareth-25 | 0.57 |
| Trideceth-2 carboxamide MEA | 0.85 |
| Glycerine | 0.5 |
| Stabilising agents, sequestering agents | Qs |
| phosphoric Acid | Qs pH = 2 |
| Water | Qs 100 |

The compositions A1 or A2 were mixed together with the compositions B and C at the time of use in the following proportions: 10 g of composition A1 or A2 with 4 g of composition B and 15 g of composition C. The mixture was applied to naturally colored hair having a tone height of 4 and to naturally colored hair having a tone height of 6. After a leave-on time of 30 minutes, the hair was rinsed, washed with a standard shampoo and dried.

The color of the hair was determined by using the L*a*b* system, with a Datacolor SF600X Spectraflash (illuminant D65, angle 10°, specular components included).

According to this system, L indicates the lightness. The lower the value of L, the more intense the color of the hair. The chromaticity coordinates are expressed by the parameters a* and b*, a* indicating the axis of red/green shades and b the axis of yellow/blue shades.

Chromaticity:

For each colored lock, the chromaticity was evaluated according to the following formula:

$$C^* = \sqrt{(a^*)^2 + (b^*)^2}$$

| Hair type | Mixture | a* | b* | C* |
|---|---|---|---|---|
| HT4 | A1 + B + C | 8.41 | 7.13 | 11.03 |
| | A2 + B + C (inventive) | 9.85 | 9.26 | 13.52 |
| HT6 | A1 + B + C | 14.61 | 14.78 | 20.78 |
| | A2 + B + C (inventive) | 15.40 | 17.15 | 23.04 |

With the two types of hair, the compositions obtained from A2 provided a higher chromaticity than the one obtained with A1.

Example 3

The following compositions were prepared:
Compositions A3 and A4 (amount expressed in grams):

| | A3 | A4 (inventive) |
|---|---|---|
| isopropyle Myristate | 52 | 87 |
| Oleth-10 | 10 | 10 |
| Disteardimonium hectorite | 2.25 | 2.25 |
| propylene Carbonate | 0.75 | 0.75 |
| water | 35 | — |

Composition B' (amount expressed in grams):

| | |
|---|---|
| dimethanesulfonate 2,3-diamino-6,7-dihydro-1H,5H-pyrazolo[1,2-A]pyrazol-1-one | 5.017 |
| 2,4-diaminophénoxyethanol•2HCl | 3.4945 |
| Hydroxyethyl cellulose (Natrosol 250 HHR) | 1.5 |
| Dipropylene glycol | 3 |
| Hexylene glycol | 3 |
| Propylene glycol | 6.2 |
| Monoethanolamine | 16.81 |
| Ethanol | 8.25 |
| Reducing agents. sequestring agents | qs |
| Water | Qs 100 |

Composition C (amount expressed in grams):

| | |
|---|---|
| hydrogen Peroxide | 6 |
| cetearylique Alcohol | 2.28 |
| Ceteareth-25 | 0.57 |
| Trideceth-2 carboxamide MEA | 0.85 |
| Glycerin | 0.5 |
| Stabilizing agents, sequestering agents | Qs |
| phosphoric Acid | Qs pH = 2 |
| Water | Qs 100 |

The compositions A2 or A3 were mixed together with the compositions B' and C at the time of use in the following proportions: 10 g of composition A3 or A4 with 4 g of composition B' and 15 g of composition C.

The resulting mixture were then applied on medium sensitized hair (SA21) and highly sensitized hair (SA42) (14.5 g of the mixture for 1 g of hair). After a leave-on time of 30 minutes. the hair was rinsed. washed with a standard shampoo and dried.

The color of the hair was determined by using the Datacolor SF600X Spectraflash (illuminant D65, angle 10°, specular components included).

Selectivity

The color was evaluated using the L*a*b* system. The selectivity of the coloration is the variation of the color between the medium sensitized colored hair and the highly sensitized colored hair. The selectivity ΔE is calculated according to the following formula:

$$\Delta E = \sqrt{(L^* - L_o^*)^2 + (a^* - a_o^*)^2 + (b^* - b_o^*)^2}$$

wherein L* indicates lightness and a* and b* are the chromaticity coordinates of the highly sensitized colored locks whereas $L_o^*$ indicates the lightness and $a_o^*$ and $b_o^*$ are the chromaticity of the medium sensitized colored locks. The

| mixture | Hair type | L* | a* | b* | ΔE |
|---|---|---|---|---|---|
| A3 + B' + C | SA21 | 19.81 | 9.17 | 3.45 | 6.11 |
|  | SA42 | 20.51 | 14.89 | 5.47 |  |
| A4 + B' + C | SA21 | 19.72 | 9.49 | 3.45 | 2.27 |
| (inventive) | SA42 | 19.58 | 11.60 | 4.27 |  |

The composition resulting from the mixture with A4 provided a color less selective than the one obtained with the mixture A3.

What is claimed is:

1. A composition for the oxidation dyeing of keratin fibers comprising:
A) at least one fatty substance wherein the at least one fatty substance is present in an amount greater than or equal to 25% by weight relative to the total weight of the composition;
B) at least one oxidation base chosen from diaminopyrazolones and acid-addition salts thereof;
C) at least one additional dye precursor other than the oxidation base in B);
D) at least one oxidizing agent; and optionally
E) at least one alkaline agent.

2. The composition of claim 1, wherein the at least one fatty substance is chosen from compounds that are liquid or pasty at room temperature and at atmospheric pressure.

3. The composition of claims 1, wherein the at least one fatty substance is different from fatty acids.

4. The composition of claim 1, wherein the at least one fatty substance is chosen from lower alkanes, fatty alcohols, fatty acid esters, fatty alcohol esters, oils and waxes.

5. The composition of claim 1, wherein the at least one fatty substance is non-silicone.

6. The composition of claim 1, wherein the at least one oxidation base is chosen from 4,5-diaminopyrazolone bases.

7. The composition of claim 1, wherein the at least one oxidation base is chosen from those of formula (I) and the acid-addition salts thereof:

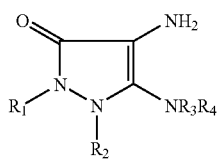

(I)

wherein:
$R_1$, $R_2$, $R_3$ and $R_4$, which may be identical or different, are independently chosen from:
a hydrogen atom;
a linear or branched $C_1$-$C_{10}$ alkyl group optionally substituted with at least one group chosen from $OR_5$, $NR_6R_7$, carboxyl, sulfonic groups, carboxamido $CONR_6R_7$, sulfonamido $SO_2NR_6R_7$, aliphatic heterocycles, and aryls optionally substituted with at least one group chosen from $C_1$-$C_4$ alkyl, hydroxyl, $C_1$-$C_2$ alkoxy, amino, and (di) ($C_1$-$C_2$)alkylamino groups;
an aryl group optionally substituted with at least one group chosen from $C_1$-$C_4$ alkyl, hydroxyl, $C_1$-$C_2$ alkoxy, amino, and (di) ($C_1$-$C_2$)alkylamino groups; and
a 5- or 6-membered heteroaryl group, optionally substituted with at least one group chosen from $C_1$-$C_4$ alkyl and $C_1$-$C_2$ alkoxy groups;
$R_5$, $R_6$ and $R_7$, which may be identical or different, are independently chosen from:
a hydrogen atom;
a linear or branched $C_1$-$C_4$ alkyl group optionally substituted with at least one group chosen from hydroxyl, $C_1$-$C_2$ alkoxy, carboxamido $CONR_8R_9$, sulfonyl $SO_2R_8$, and aryl groups optionally substituted with a $C_1$-$C_4$ alkyl, hydroxyl, $C_1$-$C_2$ alkoxy, amino or (di) ($C_1$-$C_2$)alkylamino group;
an aryl group optionally substituted with at least one group chosen from $C_1$-$C_4$ alkyl, hydroxyl, $C_1$-$C_2$ alkoxy, amino and (di) ($C_1$-$C_2$)alkylamino groups;
a carboxamido group $CONR_8R_9$; and
a sulfonyl group $SO_2R_8$;
$R_8$ and $R_9$, which may be identical or different, are independently chosen from a hydrogen atom, and a linear or branched $C_1$-$C_4$ alkyl group, optionally substituted with at least one group chosen from hydroxyl and $C_1$-$C_2$ alkoxy groups;
in addition, $R_1$ and $R_2$, and/or $R_3$ and $R_4$, independently, combine to form, together with the nitrogen atom(s) to which they are attached, a saturated or unsaturated 5- to 7-membered heterocycle, optionally substituted or N-substituted with at least one group chosen from halogen, amino, (di) ($C_1$-$C_4$)alkylamino, (di)hydroxy($C_1$-$C_2$)alkylamino, hydroxyl, carboxyl, carboxamido, (di) ($C_1$-$C_2$)alkylcarboxamido, $C_1$-$C_2$ alkoxy and $C_1$-$C_4$ alkyl groups optionally substituted with at least one group chosen from hydroxyl, amino, (di)alkylamino, alkoxy, carboxyl and sulfonyl groups; wherein said heterocycles independently formed by $R_1$ and $R_2$, and/or $R_3$ and $R_4$, with the nitrogen atoms to which they are attached, may be identical or different, and the chain members forming said heterocycles are chosen from carbon, nitrogen and oxygen.

8. The composition of claim 7, wherein $R_1$, $R_2$, $R_3$ and $R_4$, which may be identical or different, are independently chosen from a linear or branched $C_1$-$C_{10}$ alkyl group optionally substituted with piperidine.

9. The composition of claim 7, wherein $R_1$, $R_2$, $R_3$ and $R_4$, which may be identical or different, are independently chosen from a linear or branched $C_1$-$C_6$ alkyl group optionally substituted with at least one group chosen from $OR_5$, $NR_6R_7$, carboxyl, sulfonic groups, carboxamido $CONR_6R_7$, sulfonamido $SO_2NR_6R_7$, aliphatic heterocycles, and aryls optionally substituted with at least one group chosen from $C_1$-$C_4$ alkyl, hydroxyl, $C_1$-$C_2$ alkoxy, amino, and (di)($C_1$-$C_2$)alkylamino groups.

10. The composition of claim 9, wherein $R_1$, $R_2$, $R_3$ and $R_4$, which may be identical or different, are independently of chosen from a linear or branched $C_1$-$C_6$ alkyl group optionally substituted with piperidine.

11. The composition of claim 7, wherein $R_5$, $R_6$ and $R_7$, which may be identical or different, are independently chosen from a linear or branched $C_1$-$C_2$ alkyl group optionally substituted with at least one group chosen from hydroxyl, $C_1$-$C_2$ alkoxy, carboxamido $CONR_8R_9$, sulfonyl $SO_2R_8$, and aryl groups optionally substituted with a $C_1$-$C_4$ alkyl, hydroxyl, $C_1$-$C_2$ alkoxy, amino or (di)($C_1$-$C_2$)alkylamino group.

12. The composition of claim 1, wherein the at least one oxidation base is chosen from 2,3-diamino-6,7-dihydro-1H, 5H-pyrazolo[1,2-a]pyrazol-1-one and salts thereof.

13. The composition of claim 1, wherein the at least one additional dye precursor is chosen from oxidation bases other than diaminopyrazolones and couplers.

14. The composition of claim 13, wherein the at least one additional dye precursor is chosen from ortho- and para-phenylenediamine oxidation bases, ortho- and para-aminophenols, heterocyclic bases other than diaminopyrazolones, and acid-addition salts thereof.

15. The composition of claim 14, wherein the at least one additional dye precursor is chosen from para-aminophenol oxidation bases, heterocyclic bases other than diaminopyrazolones, and acid-addition salts thereof.

16. The composition of claim 13, wherein the at least one additional dye precursor is chosen from meta-aminophenol, meta-phenylenediamine, meta-diphenol and naphthol couplers, and heterocyclic couplers, and acid-addition salts thereof.

17. The composition of claim 16, wherein the at least one additional dye precursor is chosen from meta-aminophenol and meta-phenylenediamine couplers.

18. The composition of claim 1, wherein the at least one oxidizing agent is a peroxide.

19. The composition of claim 18, wherein the at least one oxidizing agent is hydrogen peroxide.

20. The composition of claim 1, wherein the at least one alkaline agent is chosen from ammonia and alkanolamine.

21. The composition of claim 20, wherein the at least one alkaline agent is an alkanolamine.

22. A process for dyeing keratin fibers comprising:
providing a composition comprising:
A) at least one fatty substance wherein the at least one fatty substance is present in an amount greater than or equal to 25% by weight relative to the total weight of the composition;
B) at least one oxidation base chosen from diaminopyrazolones and acid-addition salts thereof;
C) at least one additional dye precursor other than the oxidation base in B);
D) at least one oxidizing agent; and optionally
E) at least one alkaline agent; and
applying the composition to the keratin fibers for a time that is sufficient to develop a desired coloration.

23. A multi-compartment device comprising:
a first compartment comprising (A) at least one fatty substance;
a second compartment comprising (B) at least one oxidation base chosen from diaminopyrazolones and acid-addition salts thereof, (C) at least one additional dye precursor other than the at least one oxidation base in (B), and optionally (E) at least one alkaline agent; and
a third compartment comprising (D) at least one oxidizing agent and optionally at least one fatty substance.

24. A multi-compartment device comprising:
a first compartment comprising a composition comprising (A) at least one fatty substance and (D) at least one oxidizing agent; and
a second compartment comprising (B) at least one oxidation base chosen from diaminopyrazolones and acid-addition salts thereof, (C) at least one additional dye precursor other than the oxidation base in (B), and optionally (E) at least one alkaline agent.

25. A multi-compartment device comprising:
a first compartment comprising a composition comprising (A) at least one fatty substance, (B) at least one oxidation base chosen from diaminopyrazolones and acid-addition salts thereof, (C) at least one additional dye precursor other than the at least one oxidation base in (B), and optionally (E) at least one alkaline agent; and
a second compartment comprising (D) at least one oxidizing agent.

* * * * *